United States Patent
Cheng

(10) Patent No.: US 9,896,426 B2
(45) Date of Patent: Feb. 20, 2018

(54) EXTRACTION SEPARATION METHOD OF A FLAVONE COMPONENT BASED ON GRAPHENE

(71) Applicant: Shenzhen Violin Technology Co., Ltd., Shenzhen (CN)

(72) Inventor: Jinsheng Cheng, Foshan (CN)

( * ) Notice: Subject to any disclaimer, the term of this patent is extended or adjusted under 35 U.S.C. 154(b) by 0 days.

(21) Appl. No.: 14/948,248

(22) Filed: Nov. 21, 2015

(65) Prior Publication Data

US 2016/0145229 A1   May 26, 2016

(30) Foreign Application Priority Data

Nov. 25, 2014 (CN) .......................... 2014 1 0681182

(51) Int. Cl.
*C07D 311/30*   (2006.01)

(52) U.S. Cl.
CPC .................................. *C07D 311/30* (2013.01)

(58) Field of Classification Search
CPC .................................................. C07D 311/30
See application file for complete search history.

(56) References Cited

PUBLICATIONS

Verma, A.K., et al. "The biological potential of flavones." Nat. Prod. Rep. (2010), vol. 27, pp. 1571-1593.*

Balunas, M.J., et al. "Natural Products as Aromatase Inhibitors." Anticancer Agents Med. Chem. (Aug. 2008), vol. 8(6), pp. 1-69.*
Tapas, A.R., et al. "Flavonoids as Nutraceuticals: A Review." Trop. J. Pharm. Res. (Sep. 2008), vol. 7 (3), pp. 1089-1099.*
Khadem, S., et al. "Chromone and Flavonoid Alkaloids: Occurrence and Bioactivity." Molecules. (2012), vol. 17, pp. 191-206.*
Sereshti, H., et al. "Preparation and application of magnetic graphene oxide coated with a modified chitosan pH-sensitive hydrogel: an efficient biocompatible adsorbent for catechin." Royal Society of Chemistry. © Dec. 10, 2014. Available from: < http://pubs.rsc.org/en/content/articlepdf/2012/ra/c4ra11572d >.*
Nagao, T., et al. "Ingestion of a tea rich in catechins leads to a reduction in body fat and malondialdehyde-modified LDL in men." Am. J. Clin. Nutr. (2005), vol. 81, pp. 122-129.*

\* cited by examiner

*Primary Examiner* — Noble E Jarrell
*Assistant Examiner* — John S Kenyon
(74) *Attorney, Agent, or Firm* — Wayne & Ken, LLC; Tony Hom

(57) ABSTRACT

The present invention refers to the technical field of flavone component extraction, and provides an extraction separation method of a flavone component based on amination graphene. The flavone components comprise flavones, flavanols, isoflavones, flavanones, flavanonols, flavanones, anthocyanidins, chalcones, and chromones etc. The extraction separation method is adsorption extraction, and amination graphene is taken as a medium of adsorption extraction. The extraction separation method of the flavone components based on amination graphene is superior in separation speed and product purity, low cost and convenient operation.

7 Claims, No Drawings

EXTRACTION SEPARATION METHOD OF A FLAVONE COMPONENT BASED ON GRAPHENE

CROSS-REFERENCE TO RELATED APPLICATIONS

This application is a continuation in part of, and claims priority to, Chinese Patent Application No. 201410681182.3 with a filing date of Nov. 25, 2014. The content of the aforementioned application, including any intervening amendments thereto, is incorporated herein by reference.

TECHNICAL FIELD

The present invention refers to the technical field of flavone component extraction, more particularly, to an extraction separation method of a flavone component based on amination graphene.

BACKGROUND OF THE PRESENT INVENTION

Flavonoids, a large class of compounds widely existed in the nature, are a class of derivative yellow pigment whose parent nucleus is flavone(2-phenylchromone), characterized in that it is with basic framework of C6-C3-C6. Flavonoids can be divided into dozens of categories, flavones, flavanols, isolavones, flavanones, flavanonols, flavanones, anthocyanidins, chalcones and chromones etc., over 4000 kinds of flavonoids are found at present, mainly existed in the leaves, fruits, roots and skin of plants.

The study on flavonoids has become a hot topic in Chinese and foreign medical profession due to its high pharmaceutical value. As a kind of natural drug with broad development prospect, it has large application foreground in fields like medicine and food. These compounds can be used to prevent and cure cardiovascular and cerebrovascular diseases, such as the decrease of fragility of blood vessels, improvement of permeability of blood vessels, decrease of blood fat and cholesterol, prevention and cure of elderly hypertension, cerebral hemorrhage coronary heart disease angina and pectoris, expansion of coronary artery and promotion of coronary blood flow. Many flavone components have the activity of antitussive, anti-inflammatory, antiasthmatic and antibiosis, meanwhile, they have effects of liver protection, detoxification in the liver, anti-fungus, treatment of acute and chronic hepatitis, liver cirrhosis, anti-free radical and antioxidation. Besides, flavonoids have same effects with phytoestrogen, and can be good applied in fields like medicine and health care products.

Traditional extraction methods of flavonoids include ultrafiltration, enzymolysis approach, adsorption method by coarse pored resin, supercritical fluid extraction, ultrasonic method and microwave extraction method etc. But above traditional methods have problems like low extraction efficiency and high cost, so they can't be scalable to popularize and apply.

SUMMARY OF THE PRESENT INVENTION

To solve the problems in existing technologies, the present invention provides an extraction separation method of the flavone component based on amination graphene, combined with the situation of flavone component separation. It possess superior separation speed and product purity, low cost and convenient operation.

The content of the present invention is as follows.

An extraction separation method of a flavone component based on amination graphene, wherein the flavone components comprise flavones, flavanols, isoflavones, flavanones, flavanonols, flavanones, anthocyanidins, chalcones, and chromones etc. The extraction separation method is adsorption extraction, and amination graphene is taken as a medium of adsorption extraction.

Graphene is a new material with single-layered sheet structure made up of carbon atom and a flat film of hexagon honeycomb lattice made up of carbon atom with $sp^2$ hybrid orbital. As the two-dimensional material whose thickness is the same with that of carbon atom, it is the known thinnest and hardest nano material in the world. It is of promising application with large surface specific area, excellent mechanical property and good heat conductivity. The surface of amination graphene will combine with rich amine terminated for the faintly alkalinity of amination graphene by the amination of graphene. And flavonoids are of mass phenolic hydroxyl groups, faintly acidity and easy soluble to alkaline water, they can be precipitated after acidification. So it is feasible to perform adsorption separation on flavonoids by amination graphene. Moreover, the ring opening of flavone parent nucelus of flavonoids will be performed under alkaline condition to form 2'-hydroxychalcone, the polarity will rise, thereby accelerating dissolution. So it can be leached by alkaline sodium carbonate, sodium hydroxide, calcium hydroxide water solution or diluted alkaline alcohol (like 50% ethanol), and the flavonoids are precipitated by acidifying leach liquor. Besides, the adsorption separation effect between flavonoids with faintly acidity and amination graphene can be further improved due to the ultra large specific surface area (2630 $m^2$/g in theory) of graphene material.

Furthermore, the amination graphene is prepared by surface aminated modification of renewable resources derived graphene which is prepared by modified Hummers methods.

Furthermore, there are unmodified and modified amination graphene, the modified amination graphene include amination graphene oxide, aminated boron-doped graphene, aminated nitrogen-doped graphene, animated graphdiyne, animated carbon nanotube, animated fullerenes, chitosan-graphene composite membrane, chitosan-graphene oxide, metal particles/chitosan-graphene, amination graphene-ionic liquid, amination graphene-ionic liquid oxide and graphene-ionic liquid.

Furthermore, the ionic liquid of amination graphene-ionic liquid and the amination graphene-ionic liquid oxide include at least one from 1-ethyl-3-methylimidazolium hexafluorophosphate, 1-ethyl-3-methylimidazolium bis[(trifluoromethyl)sulfonyl]imide, 1-butyl-3-methylimidazolium bis[(trifluoromethyl)sulfonyl]imide, 1-butyl-3-methylimidazolium tetrafluoroborate, 1-butyl-3-methylimidazole chloride, 1-butyl-3-methylimidazolium bromide, 1-hexylpyridinium trifluoromethanesulfonate, 1-ethyl-3-methylimidazolium bromide,1-ethyl-3-methylimidazolium-Iodide, 1-butyl-3-methylimidazolium hexafluorophosphate, 1-butyl-3-methylimidazolium bis[(trifluoromethyl)sulfonyl]imide, 1-ethyl-3-methylimidazoliumte-trafluoroborate, 1,2-dimethyl-3-propylimidazolium bis(trifluoromethylsulfonyl)imide, 1-ethyl-3-methylimidazolium p-toluenesulfonate, 1-(cyanomethyl)pyridinium chloride, 1-ethyl-3-methylimidazolium hexafluorophosphate, 1-hexylpyridinium hexafluorophosphate, 1-butyl-2,3-dimethylimidazolium hexafluorophosphate, 1-hexyl-3-methylimidazolium hexafluorophosphate, trihexyl(tetradecyl)phosphonium hexafluorophosphate, 1-butyl-3-methylimidazolium tetrafluoroborate,1-butyl-3-methylimidazolium chloride, 1-butyl-3-dimethylimidazolium diethyleneglycolmonomethylether sulfate, 1-butyl-3-methylimidazolium methanesulfonate, 1-butyl-3-methylimidazolium octyl sulfate, 1-butyl-3-methylimidazolium hexafluorophosphate, 1-aminopyridinium Iodide, 1,2-bis (3-methylimidazolium-1-yl)ethane dihydroxide, 1-butyl-3-methylimidazolium hydroxide, 1-methyl-3-butylimidazolium hydroxide, and 1-(cyanomethyl)pyridinium chloride.

Furtherly, the ionic liquid of the graphene-basic ionic liquid include at least one from 1-aminopyridinium Iodide, 1,2-Bis (3-methylimidiazolium-1-yl)ethane dihydroxide, 1-butyl-3-methylimidazolium hydroxide, 1-methyl-3-butylimidazolium hydroxide, 1-(cyanomethyl)pyridinium chloride, and 1-butyl-3-methylimidazolium hydroxide.

Furtherly, the metal particles of metal particles/chitosan-graphene include transition element and main group element.

Furtherly, the amino modified groups include ethylenediamine, triethylene tetramine, octadecylamine, dodecylamine, hydrazine hydrate, hydroxylamine, ammonia, p-chloroaniline, sec-butylamine, dodecyl-tetradecyl dimethyl amine, nitrogen amino acid, protein, and polyamidoamine (PAMAM) dendrimer.

Furtherly, the plants include ginkgoaceae, rutaceae, ericaceae, labiatae, umbelliferae, leguminosae, theaceae, meliaceae, compositae, moraceae, ericaceae and caprifoliaceae etc.

Furtherly, the plants include ginkgo leaf, *Rosa roxbunghii*, *Camellia nitidissima* Chi, tea tree (tea, green tea, pu'er tea, dark tea etc.), high mountain tea, moyeam tea, *camellia sasanqua*, sky-fruit, lemon, hawthorn, pomegranate, soybean, mango, licorice, *Trifolium pratense* L., blueberry, grape, cauliflower, *Lobed kudzuvine* root, mulberry twig, celery and honeysuckle etc.

Furtherly, the a s of adsorption separation of plants are a flower, fruit or rhizome.

The advantages of the present invention are as follows.

Firstly, superior separation speed. The amination graphene is used as the carrier material of adsorption separation, so the faintly alkaline amination graphene and the faintly acid flavone components can be combined to give full play to the advantages of graphene material, that is, large specific surface area and alkalescence, thereby accelerating separation speed effectively;

Secondly, superior product purity. Interference of other components can be effectively removed by performing selective absorption separation faintly alkaline flavone component through acid-base adsorption;

Thirdly, low cost. The separation cost can be reduced effectively because of its no huge equipment investment, much more sources of raw material and recycling of carrier material, that is, the amination graphene;

Fourthly, convenient operation. The convenience of operation is improved because of its simple equipment operation, conventional chemical operation and simplified operation procedure.

DETAILED DESCRIPTION OF PREFERRED EMBODIMENTS

For better understanding of the present invention, the following is detailed description about summary and embodiments of the present invention.

An extraction separation method of a flavone component based on amination graphene, wherein the extraction separation method is adsorption extraction, and amination graphene is taken as the medium of adsorption extraction. For good effect of adsorption separation, it is operated as follows in general in actual operation.

The first step preparation of plant concentrate. The leaves, flowers, fruits or rhizomes of ginkgoaceae, rutaceae, ericaceae, labiatae, umbelliferae, leguminosae, theaceae, meliaceae, compositae, moraceae, encaceae and caprifoliaceae plants with flavonoids were picked, and the plants include ginkgo leaf, *Rosa roxbunghii*, *Camellia nitidissirna* Chi, tea tree (tea, green tea, pu'er tea, dark tea etc.), high mountain tea, moyeam tea, *Camellia sesanqua*, sky-fruit, lemon, hawthorn, pomegranate, soybean, mango, licorice, *Trifolium pratense* L., blueberry, grape, cauliflower, *lobed kudzuvine* root, mulberry twig, celery and honeysuckle etc. and the freshest and highest quality parts were selected as per *Pharmacopoeia of China*(2010) and smashed by medicine herbs grinder after washing and drying, acetone (over 95%) was added and extracted for 5-6 h by Soxhlet extractor to obtain extract A; about 3 L of acetone (over 95%) was added into extracted residue and ultrasound was performed for 1.5 h under 40-60° C. to obtain the extract B; the extract A and extract B was mixed, then the acetone solvent was evaporated by rotary evaporation of rotary evaporators and finally the plant concentrate of flavonoids with organic phase was obtained.

The second step: adsorption extraction. Some amination graphene materials were added into the plant concentrate prepared by above step, there were unmodified and modified amination graphene, the modified amination graphene included amination graphene oxide, aminated boron-doped graphene, aminated nitrogen-doped graphene, animated graphdiyne, animated carbon nanotube, animated fullerenes, chitosan-graphene composite membrane, chitosan-graphene oxide, metal particles/chitosan-graphene, amination graphene-ionic liquid, amination graphene-ionic liquid oxide and graphene-ionic liquid. Amination graphene material was added into the plant concentrate and transferred into the ultrasonic machine for performing ultrasonic extraction for 2 h under 400 W, in a successive step, the plant concentrate was filtrated with 0.2 μm microporous membrane and washed for several times with deionized water and ethanol, and other ions or organics of physical adsorption were removed, then the black solid adsorbed with flavonoids was obtained.

The third step, washing separation. The obtained black solid in the second step was dispersed into deionized water again and the pH value was adjusted to be less than 7, the binding force of amination graphene with faintly alkality and flavonoids with faintly acidity weakened to separate gradually. Then some acetone were added into the deionized water dispersion liquid with black solid immersion and ultrasonic extraction was performed for 1 h, so the flavonoids can be extracted into the acetone phase. The acetone phase was separated, and the acetone was removed by evaporation and dried by anhydrous sodium sulfate, then the final flavonoids product was obtained after separation. Finally, the obtained flavone components comprise flavones, flavanols, isoflavones, flavanones, flavanonols, flavanones, anthocyanidins, chalcones, and chromones etc.

After separation, the dispersion liquid with amination graphene immersion was adjusted to faintly alkalinity again, then the dispersion was filtrated, washed repeatedly with deionized water, vaccum dried for 24 h in room temperature and activated, in this way, it can be recycled for subsequent use.

To reduce the cost effectively, the amination graphene is prepared by surface aminated modification of renewable resources derived graphene, for example, straw, bagasse and cornstalk, together with successive modified Hummers methods Moreover, to meet different usage requirements, the ionic liquid of amination graphene ionic liquid and the amination graphene-ionic liquid oxide at least one from 1-ethyl-3-methylimidazolium hexafluorophosphate, 1-ethyl-3-methyl-imidazolium bis[(trifluoromethyl)sulfonyl]imide, 1-butyl-3-methylimidazolium bis[(trifluoromethyl)sulfonyl]imide, 1-butyl-3-methylimidazolium tetrafluoroborate, 1-butyl-3-methylimidazole chloride, 1-butyl-3-methylimidazolium bromide, 1-hexylpyridinium trifluoromethanesulfonate, 1-ethyl-3-methylimidazolium bromide,1-ethyl-3-methyl-imidazolium-Iodide, 1-butyl-3-methylimidazolium hexafluorophosphate, 1-butyl-3-methyli-midazolium bis[(trifluoromethyl)sulfonyl]imide, 1-ethyl-3-methylimidazoliumte-trafluoroborate, 1,2-dimethyl-3-propylimidazolium bis(trifluoromethylsulfonyl)imide, 1-ethyl-3-methylimidazolium p-toluenesulfonate, 1-(cyanomethyl)pyridinium chloride, 1-ethyl-3-methylimidazolium hexafluorophosphate, 1-hexylpyridinium hexafluorophosphate, 1-butyl-2,3-dimethylimidazolium hexafluorophosphate, 1-hexyl-3-methylimidazolium hexafluorophosphate, trihexyl(tetradecyl)phosphonium hexafluorophosphate, 1-butyl-3-methylimidazolium tetrafluoroborate, 1-butyl-3-methylimidazolium chloride, 1-butyl-3-dimethylimidazolium diethyleneglycolmonomethylether sulfate, 1-butyl-3-methylimidazolium methanesulfonate, 1-butyl-3-methylimidazolium octyl sulfate, 1-butyl-3-methylimidazolium hexafluorophosphate,1-aminopyridinium Iodide, 1,2-bis (3-methylimidazolium-1-yl)ethane dihydroxide, 1-butyl-3-methylimidazolium hydroxide, 1-methyl-3-butylimidazolium hydroxide, and 1-(cyanomethyl)pyridinium chloride etc.

And to meet different usage requirements, the ionic liquid of the graphene-basic ionic liquid include at least one from 1-aminopyridinium Iodide, 1,2-bis(3-methylimidazolium-1-yl)ethane dihydroxide, 1-butyl-3-methylimidazolium hydroxide, 1-methyl-3-butylimidazolium hydroxide, 1-(cyanomethyl)pyridinium chloride, and 1-butyl-3-methylimidazolium hydroxide etc.

Moreover, to meet different usage requirements, the metal particles of metal particles/chitosan-graphene include transition element and main group element.

Moreover, to meet different usage requirements, the amino modified groups include ethylenediamine, triethylene tetramine, octadecylamine, dodecylamine, hydrazine hydrate, hydroxylamine, ammonia, p-chloroaniline, sec-butylamine, dodecyl-tetradecyl dimethyl amine, nitrogen amino acid, protein, and polyamidoamine (PAMAM) dendrimer.

The above disclosure merely shows several specific embodiments of the present invention, and the present invention is not limited thereto; those ordinary skilled in the art complete the implementation of the present invention without difficulty based on the description and above disclosure; while it should be noted to those skilled in the art that several variations, modification and improvements can also be made within the scope of technical proposal, and these variations, modification and improvements are equivalent embodiments; moreover, they are also considered within the protective scope of the present invention.

I claim:

1. A method for extraction and separation of a flavone component, comprising:
    modifying graphene to prepare an amination graphene;
    adsorbing and extracting the flavone component with the amination graphene;
    wherein the flavone component is selected from a group comprising flavones, flavanols, isoflavones, flavanonols, flavanones, anthocyanidins, chalcones and chromones.

2. The method of claim 1, wherein the amination graphene is an amination graphene-ionic liquid or an amination graphene-ionic liquid oxide which comprises an ionic liquid selected from a group comprising 1-ethyl-3-methylimidazolium hexafluorophosphate, 1-ethyl-3-methylimidazolium bis[(trifluoromethyl)sulfonyl]imide, 1-butyl-3-methylimidazolium bis[(trifluoromethyl)sulfonyl]imide, 1-butyl-3-methylimidazolium tetrafluoroborate, 1-butyl-3-methylimidazole chloride, 1-butyl-3-methylimidazolium bromide, 1-hexylpyridinium trifluoromethanesulfonate, 1-ethyl-3-methylimidazolium bromide, 1-ethyl-3-methylimidazolium-Iodide, 1-butyl-3-methylimidazolium hexafluorophosphate, 1-butyl-3-methyli-midazolium bis[(trifluoromethyl)sulfonyl]imide, 1-ethyl-3-methylimidazoliumte-trafluoroborate, 1,2-dimethyl-3-propylimidazolium bis(trifluoromethylsulfonyl)imide, 1-ethyl-3-methylimidazolium p-toluenesulfonate, 1-(cyanomethyl)pyridinium chloride, 1-hexylpyridinium hexafluorophosphate, 1-butyl-2,3-dimethylimidazolium hexafluorophosphate, 1-hexyl-3-methylimidazolium hexafluorophosphate, trihexyl(tetradecyl)phosphonium hexafluorophosphate, 1-butyl-3-methylimidazolium chloride, 1-butyl-3-dimethylimidazolium diethyleneglycolmonomkethylether sulfate, 1-butyl-3-methylimidazolium methanesulfonate, 1-butyl-3-methylimidazolium octyl sulfate, 1-aminopyridinium Iodide, 1,2-bis (3-methylimidazolium-1-yl) ethane dihydroxide, 1-butyl-3-methylimidazolium hydroxide, 1-methyl-3-butylimidazolium hydroxide, and 1-(cyanomethyl)pyridinium chloride.

3. The method of claim 2, wherein the ionic liquid of the graphene-basic ionic liquid comprises at least one from 1-aminopyridinium Iodide, 1,2-bis(3-methylimidazolium-1-yl)ethane dihydroxide, 1-methyl-3-butylimidazolium hydroxide, 1-(cyanomethyl)pyridinium chloride, and 1-butyl-3-methylimidazolium hydroxide.

4. The method of claim 3, wherein the amination graphene is modified by at least one of ethylenediamine, triethylene tetramine, octadecylamine, dodecylamine, hydrazine hydrate, hydroxylamine, ammonia, p-chloroaniline, sec-butylamine, dodecyl-tetradecyl dimethyl amine, nitrogen amino acid, protein, and polyamidoamine (PAMAM) dendrimer.

5. The method of claim 1, wherein the flavone component is adsorbed from plants;
    the plants comprise ginkgoaceae, rutaceae, ericaceae, labiatae, umbelliferae, leguminosae, theaceae, meliaceae, compositae, moraceae and caprifoliaceae.

6. The method of claim 5, wherein the plants comprise ginkgo leaf, *Rosa roxbunghii, Camellia nitidissima* Chi, black tea, green tea, pu'er tea, dark tea, high mountain tea, moyeam tea, *Camellia sasanqua*, sky-fruit, lemon, hawthorn, pomegranate, soybean, mango, licorice, *Trifolium pratense* L., blueberry, grape, cauliflower, *Lobed kudzuvine* root, mulberry twig, celery and honeysuckle.

7. The method of claim 6, wherein in the step of adsorbing the flavone component with amination graphene, the flavone component is adsorbed from leaves, flowers, fruits or rhizomes of the plants.

* * * * *